(12) United States Patent
Dietz

(10) Patent No.: US 8,419,759 B2
(45) Date of Patent: Apr. 16, 2013

(54) ULTRASONIC SURGICAL INSTRUMENT WITH COMB-LIKE TISSUE TRIMMING DEVICE

(75) Inventor: Timothy G. Dietz, Terrace Park, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 417 days.

(21) Appl. No.: 12/703,899

(22) Filed: Feb. 11, 2010

(65) Prior Publication Data

US 2011/0196405 A1 Aug. 11, 2011

(51) Int. Cl.
*A61B 17/32* (2006.01)

(52) U.S. Cl.
USPC ........................................................ 606/169

(58) Field of Classification Search .................. 606/167, 606/169–171, 180; 604/22; 600/562–568
See application file for complete search history.

(56) References Cited

U.S. PATENT DOCUMENTS

| | | | |
|---|---|---|---|
| 2,704,333 A | 3/1955 | Calosi et al. |
| 2,736,960 A | 3/1956 | Armstrong |
| 2,849,788 A | 9/1958 | Creek |
| RE25,033 E | 8/1961 | Balamuth et al. |
| 3,015,961 A | 1/1962 | Roney |
| 3,513,848 A | 5/1970 | Winston et al. |
| 3,526,219 A | 9/1970 | Balamuth |
| 3,614,484 A | 10/1971 | Shoh |
| 3,636,943 A | 1/1972 | Balamuth |
| 3,776,238 A | 12/1973 | Peyman et al. |
| 3,805,787 A | 4/1974 | Banko |
| 3,830,098 A | 8/1974 | Antonevich |
| 3,854,737 A | 12/1974 | Gilliam, Sr. |
| 3,862,630 A | 1/1975 | Balamuth |
| 3,900,823 A | 8/1975 | Sokal et al. |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 4,156,187 A | 5/1979 | Murry et al. |
| 4,188,927 A | 2/1980 | Harris |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

*Technology Overview*, printed from www.harmonicscalpel.com, Internet site, website accessed on Jun. 13, 2007, (3 pages).

(Continued)

*Primary Examiner* — Ryan Severson

(57) ABSTRACT

In one general aspect, various embodiments are directed to an ultrasonic surgical instrument that has an ultrasonic blade that protrudes from at least one ultrasonic transducer that is movably supported within a handle housing. The ultrasonic blade protrudes through an outer sheath assembly that is attached to the handle housing. A distal end portion of the outer sheath has at least one comb-like portion formed thereon. In some embodiments, a distal end of the ultrasonic blade is axially movable adjacent to the at least one comb-like portion. In other embodiments, the distal end of the ultrasonic blade is rotatable adjacent to the at least one comb-like portion.

20 Claims, 5 Drawing Sheets

U.S. PATENT DOCUMENTS

| | | |
|---|---|---|
| 4,200,106 A | 4/1980 | Douvas et al. |
| 4,306,570 A * | 12/1981 | Matthews ............... 600/567 |
| 4,445,063 A | 4/1984 | Smith |
| 4,491,132 A | 1/1985 | Aikins |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,649,919 A | 3/1987 | Thimsen et al. |
| 4,708,127 A | 11/1987 | Abdelghani |
| 4,712,722 A | 12/1987 | Hood et al. |
| 4,827,911 A | 5/1989 | Broadwin et al. |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,903,696 A | 2/1990 | Stasz et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,126,618 A | 6/1992 | Takahashi et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grezezykowski |
| 5,213,569 A | 5/1993 | Davis |
| 5,221,282 A | 6/1993 | Wuchinich |
| 5,226,909 A * | 7/1993 | Evans et al. .................. 606/159 |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,275,609 A | 1/1994 | Pingleton et al. |
| 5,282,800 A | 2/1994 | Foshee et al. |
| 5,304,115 A | 4/1994 | Pflueger et al. |
| D347,474 S | 5/1994 | Olson |
| 5,322,055 A | 6/1994 | Davison et al. |
| 5,324,299 A | 6/1994 | Davison et al. |
| 5,344,420 A | 9/1994 | Hilal et al. |
| 5,346,502 A | 9/1994 | Estabrook et al. |
| 5,357,423 A | 10/1994 | Weaver et al. |
| 5,366,466 A | 11/1994 | Christian et al. |
| 5,371,429 A | 12/1994 | Manna |
| D354,564 S | 1/1995 | Medema |
| 5,381,067 A | 1/1995 | Greenstein et al. |
| 5,403,312 A | 4/1995 | Yates et al. |
| 5,411,481 A | 5/1995 | Allen et al. |
| 5,419,761 A | 5/1995 | Narayanan et al. |
| 5,421,829 A | 6/1995 | Olichney et al. |
| 5,438,997 A | 8/1995 | Sieben et al. |
| 5,449,370 A | 9/1995 | Vaitekunas |
| 5,471,988 A | 12/1995 | Fujio et al. |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,562,609 A | 10/1996 | Brumbach |
| 5,562,610 A | 10/1996 | Brumbach |
| 5,601,601 A | 2/1997 | Tal et al. |
| 5,603,773 A | 2/1997 | Campbell |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,730,752 A | 3/1998 | Alden et al. |
| 5,733,074 A | 3/1998 | Stöck et al. |
| 5,741,226 A | 4/1998 | Strukel et al. |
| 5,792,135 A | 8/1998 | Madhani et al. |
| 5,810,859 A | 9/1998 | DiMatteo et al. |
| 5,817,084 A | 10/1998 | Jensen |
| 5,827,323 A | 10/1998 | Klieman et al. |
| 5,828,160 A | 10/1998 | Sugishita |
| 5,836,897 A | 11/1998 | Sakurai et al. |
| 5,843,109 A | 12/1998 | Mehta et al. |
| 5,878,193 A | 3/1999 | Wang et al. |
| 5,879,364 A | 3/1999 | Bromfield et al. |
| 5,893,835 A | 4/1999 | Witt et al. |
| 5,897,523 A | 4/1999 | Wright et al. |
| 5,897,569 A | 4/1999 | Kellogg et al. |
| 5,906,628 A | 5/1999 | Miyawaki et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,980,510 A | 11/1999 | Tsonton et al. |
| 5,989,274 A | 11/1999 | Davison et al. |
| 5,989,275 A | 11/1999 | Estabrook et al. |
| 5,993,972 A | 11/1999 | Reich et al. |
| 6,024,741 A | 2/2000 | Williamson, IV et al. |
| 6,033,375 A | 3/2000 | Brumbach |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,110,127 A | 8/2000 | Suzuki |
| 6,113,594 A | 9/2000 | Savage |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |

| | | | | | | |
|---|---|---|---|---|---|---|
| 6,319,221 B1 | 11/2001 | Savage et al. | | 6,933,656 B2 | 8/2005 | Matsushita et al. |
| 6,325,811 B1 | 12/2001 | Messerly | | D509,589 S | 9/2005 | Wells |
| 6,328,751 B1 | 12/2001 | Beaupre | | 6,942,677 B2 | 9/2005 | Nita et al. |
| 6,340,352 B1 | 1/2002 | Okada et al. | | 6,945,981 B2 | 9/2005 | Donofrio et al. |
| 6,352,532 B1 | 3/2002 | Kramer et al. | | D511,145 S | 11/2005 | Donofrio et al. |
| 6,364,888 B1 | 4/2002 | Niemeyer et al. | | 6,976,844 B2 | 12/2005 | Hickok et al. |
| 6,379,320 B1 | 4/2002 | Lafon et al. | | 6,976,969 B2 | 12/2005 | Messerly |
| D457,958 S | 5/2002 | Dycus et al. | | 6,977,495 B2 | 12/2005 | Donofrio |
| 6,383,194 B1 | 5/2002 | Pothula | | 6,984,220 B2 | 1/2006 | Wuchinich |
| 6,387,109 B1 | 5/2002 | Davison et al. | | 7,001,335 B2 | 2/2006 | Adachi et al. |
| 6,388,657 B1 | 5/2002 | Natoli | | 7,011,657 B2 | 3/2006 | Truckai et al. |
| 6,391,042 B1 | 5/2002 | Cimino | | 7,033,357 B2 | 4/2006 | Baxter et al. |
| 6,405,733 B1 | 6/2002 | Fogarty et al. | | 7,041,083 B2 | 5/2006 | Chu et al. |
| 6,416,486 B1 | 7/2002 | Wampler | | 7,041,088 B2 | 5/2006 | Nawrocki et al. |
| 6,423,073 B2 | 7/2002 | Bowman | | 7,041,102 B2 | 5/2006 | Truckai et al. |
| 6,423,082 B1 | 7/2002 | Houser et al. | | 7,070,597 B2 | 7/2006 | Truckai et al. |
| 6,428,539 B1 | 8/2002 | Baxter et al. | | 7,074,219 B2 | 7/2006 | Levine et al. |
| 6,432,118 B1 | 8/2002 | Messerly | | 7,077,039 B2 | 7/2006 | Gass et al. |
| 6,436,114 B1 | 8/2002 | Novak et al. | | 7,077,853 B2 | 7/2006 | Kramer et al. |
| 6,436,115 B1 | 8/2002 | Beaupre | | 7,083,619 B2 | 8/2006 | Truckai et al. |
| 6,443,969 B1 | 9/2002 | Novak et al. | | 7,087,054 B2 | 8/2006 | Truckai et al. |
| 6,454,781 B1 | 9/2002 | Witt et al. | | 7,101,378 B2 | 9/2006 | Salameh et al. |
| 6,454,782 B1 | 9/2002 | Schwemberger | | 7,108,695 B2 | 9/2006 | Witt et al. |
| 6,458,142 B1 | 10/2002 | Faller et al. | | 7,112,201 B2 | 9/2006 | Truckai et al. |
| 6,480,796 B2 | 11/2002 | Wiener | | 7,118,564 B2 | 10/2006 | Ritchie et al. |
| 6,485,490 B2 | 11/2002 | Wampler et al. | | 7,124,932 B2 | 10/2006 | Isaacson et al. |
| 6,491,708 B2 | 12/2002 | Madan et al. | | 7,125,409 B2 | 10/2006 | Truckai et al. |
| 6,497,715 B2 | 12/2002 | Satou | | 7,135,018 B2 | 11/2006 | Ryan et al. |
| 6,500,176 B1 | 12/2002 | Truckai et al. | | 7,135,030 B2 | 11/2006 | Schwemberger et al. |
| 6,500,188 B2 | 12/2002 | Harper et al. | | 7,153,315 B2 | 12/2006 | Miller |
| 6,524,251 B2 | 2/2003 | Rabiner et al. | | D536,093 S | 1/2007 | Nakajima et al. |
| 6,524,316 B1 | 2/2003 | Nicholson et al. | | 7,156,189 B1 | 1/2007 | Bar-Cohen et al. |
| 6,527,736 B1 | 3/2003 | Attinger et al. | | 7,156,853 B2 | 1/2007 | Muratsu |
| 6,533,784 B2 | 3/2003 | Truckai et al. | | 7,157,058 B2 | 1/2007 | Marhasin et al. |
| 6,537,291 B2 | 3/2003 | Friedman et al. | | 7,159,750 B2 | 1/2007 | Racenet et al. |
| 6,543,452 B1 | 4/2003 | Lavigne | | 7,163,548 B2 | 1/2007 | Stulen et al. |
| 6,543,456 B1 | 4/2003 | Freeman | | 7,169,146 B2 | 1/2007 | Truckai et al. |
| 6,544,260 B1 | 4/2003 | Markel et al. | | 7,179,271 B2 | 2/2007 | Friedman et al. |
| 6,561,983 B2 | 5/2003 | Cronin et al. | | 7,186,253 B2 | 3/2007 | Truckai et al. |
| 6,572,632 B2 | 6/2003 | Zisterer et al. | | 7,189,233 B2 | 3/2007 | Truckai et al. |
| 6,575,969 B1 | 6/2003 | Rittman, III et al. | | 7,204,820 B2 | 4/2007 | Akahoshi |
| 6,582,451 B1 | 6/2003 | Marucci et al. | | 7,220,951 B2 | 5/2007 | Truckai et al. |
| 6,589,200 B1 | 7/2003 | Schwemberger et al. | | 7,223,229 B2 | 5/2007 | Inman et al. |
| 6,589,239 B2 | 7/2003 | Khandkar et al. | | 7,229,455 B2 | 6/2007 | Sakurai et al. |
| 6,610,059 B1 | 8/2003 | West, Jr. | | 7,273,483 B2 | 9/2007 | Wiener et al. |
| 6,616,450 B2 | 9/2003 | Mossle et al. | | 7,285,895 B2 | 10/2007 | Beaupré |
| 6,623,501 B2 | 9/2003 | Heller et al. | | 7,309,849 B2 | 12/2007 | Truckai et al. |
| 6,626,926 B2 | 9/2003 | Friedman et al. | | 7,311,709 B2 | 12/2007 | Truckai et al. |
| 6,633,234 B2 | 10/2003 | Wiener et al. | | 7,317,955 B2 | 1/2008 | McGreevy |
| 6,656,177 B2 | 12/2003 | Truckai et al. | | 7,326,236 B2 | 2/2008 | Andreas et al. |
| 6,662,127 B2 | 12/2003 | Wiener et al. | | 7,331,410 B2 | 2/2008 | Yong et al. |
| 6,663,941 B2 | 12/2003 | Brown et al. | | 7,353,068 B2 | 4/2008 | Tanaka et al. |
| 6,669,690 B1 | 12/2003 | Okada et al. | | 7,354,440 B2 | 4/2008 | Truckai et al. |
| 6,676,660 B2 | 1/2004 | Wampler et al. | | 7,380,695 B2 | 6/2008 | Doll et al. |
| 6,678,621 B2 | 1/2004 | Wiener et al. | | 7,380,696 B2 | 6/2008 | Shelton, IV et al. |
| 6,679,899 B2 | 1/2004 | Wiener et al. | | 7,381,209 B2 | 6/2008 | Truckai et al. |
| 6,682,544 B2 | 1/2004 | Mastri et al. | | 7,390,317 B2 | 6/2008 | Taylor et al. |
| 6,689,146 B1 | 2/2004 | Himes | | 7,404,508 B2 | 7/2008 | Smith et al. |
| 6,716,215 B1 | 4/2004 | David et al. | | 7,408,288 B2 | 8/2008 | Hara |
| 6,731,047 B2 | 5/2004 | Kauf et al. | | D576,725 S | 9/2008 | Shumer et al. |
| 6,733,506 B1 | 5/2004 | McDevitt et al. | | D578,643 S | 10/2008 | Shumer et al. |
| 6,762,535 B2 | 7/2004 | Take et al. | | D578,644 S | 10/2008 | Shumer et al. |
| 6,770,072 B1 | 8/2004 | Truckai et al. | | D578,645 S | 10/2008 | Shumer et al. |
| 6,773,443 B2 | 8/2004 | Truwit et al. | | 7,431,704 B2 | 10/2008 | Babaev |
| 6,773,444 B2 | 8/2004 | Messerly | | 7,441,684 B2 | 10/2008 | Shelton, IV et al. |
| 6,783,524 B2 | 8/2004 | Anderson et al. | | 7,455,208 B2 | 11/2008 | Wales et al. |
| 6,786,382 B1 | 9/2004 | Hoffman | | 7,472,815 B2 | 1/2009 | Shelton, IV et al. |
| 6,786,383 B2 | 9/2004 | Stegelmann | | 7,473,263 B2 | 1/2009 | Johnston et al. |
| 6,790,216 B1 | 9/2004 | Ishikawa | | 7,479,148 B2 | 1/2009 | Beaupre |
| 6,802,843 B2 | 10/2004 | Truckai et al. | | 7,479,160 B2 | 1/2009 | Branch et al. |
| 6,828,712 B2 | 12/2004 | Battaglin et al. | | 7,494,468 B2 | 2/2009 | Rabiner et al. |
| 6,869,439 B2 | 3/2005 | White et al. | | 7,503,893 B2 | 3/2009 | Kucklick |
| 6,875,220 B2 | 4/2005 | Du et al. | | 7,506,790 B2 | 3/2009 | Shelton, IV |
| 6,905,497 B2 | 6/2005 | Truckai et al. | | 7,506,791 B2 | 3/2009 | Omaits et al. |
| 6,908,472 B2 | 6/2005 | Wiener et al. | | 7,524,320 B2 | 4/2009 | Tierney et al. |
| 6,913,579 B2 | 7/2005 | Truckai et al. | | 7,534,243 B1 | 5/2009 | Chin et al. |
| 6,926,716 B2 | 8/2005 | Baker et al. | | D594,983 S | 6/2009 | Price et al. |
| 6,929,632 B2 | 8/2005 | Nita et al. | | 7,549,564 B2 | 6/2009 | Boudreaux |
| 6,929,644 B2 | 8/2005 | Truckai et al. | | 7,559,450 B2 | 7/2009 | Wales et al. |

| | | | |
|---|---|---|---|
| 7,567,012 B2 | 7/2009 | Namikawa | |
| 7,578,820 B2 | 8/2009 | Moore et al. | |
| 7,654,431 B2 | 2/2010 | Hueil et al. | |
| 7,665,647 B2 | 2/2010 | Shelton, IV et al. | |
| 7,670,334 B2 | 3/2010 | Hueil et al. | |
| 7,674,263 B2 | 3/2010 | Ryan | |
| 7,691,098 B2 | 4/2010 | Wallace et al. | |
| 7,713,202 B2 | 5/2010 | Boukhny et al. | |
| 7,714,481 B2 | 5/2010 | Sakai | |
| D618,797 S | 6/2010 | Price et al. | |
| 7,751,115 B2 | 7/2010 | Song | |
| 7,770,774 B2 | 8/2010 | Mastri et al. | |
| 7,770,775 B2 | 8/2010 | Shelton, IV et al. | |
| 7,780,054 B2 | 8/2010 | Wales | |
| 7,780,659 B2 | 8/2010 | Okada et al. | |
| 7,784,662 B2 | 8/2010 | Wales et al. | |
| 7,798,386 B2 | 9/2010 | Schall et al. | |
| 7,806,891 B2 | 10/2010 | Nowlin et al. | |
| 7,810,693 B2 | 10/2010 | Broehl et al. | |
| 7,824,401 B2 | 11/2010 | Manzo et al. | |
| 7,837,699 B2 | 11/2010 | Yamada et al. | |
| 7,854,735 B2 | 12/2010 | Houser et al. | |
| D631,155 S | 1/2011 | Peine et al. | |
| 7,861,906 B2 | 1/2011 | Doll et al. | |
| 7,876,030 B2 | 1/2011 | Taki et al. | |
| D631,965 S | 2/2011 | Price et al. | |
| 7,892,606 B2 | 2/2011 | Thies et al. | |
| 7,901,423 B2 | 3/2011 | Stulen et al. | |
| 7,905,881 B2 | 3/2011 | Masuda et al. | |
| 7,922,651 B2 | 4/2011 | Yamada et al. | |
| 7,959,050 B2 | 6/2011 | Smith et al. | |
| 7,959,626 B2 | 6/2011 | Hong et al. | |
| 7,976,544 B2 | 7/2011 | McClurken et al. | |
| 8,038,693 B2 | 10/2011 | Allen | |
| 8,061,014 B2 | 11/2011 | Smith et al. | |
| 8,089,197 B2 | 1/2012 | Rinner et al. | |
| 8,157,145 B2 | 4/2012 | Shelton, IV et al. | |
| 8,162,966 B2 | 4/2012 | Connor et al. | |
| 8,177,800 B2 | 5/2012 | Spitz et al. | |
| 8,182,502 B2 | 5/2012 | Stulen et al. | |
| D661,801 S | 6/2012 | Price et al. | |
| D661,802 S | 6/2012 | Price et al. | |
| D661,803 S | 6/2012 | Price et al. | |
| D661,804 S | 6/2012 | Price et al. | |
| 8,253,303 B2 | 8/2012 | Giordano et al. | |
| 2001/0025184 A1 | 9/2001 | Messerly | |
| 2001/0031950 A1 | 10/2001 | Ryan | |
| 2001/0039419 A1 | 11/2001 | Francischelli et al. | |
| 2002/0002377 A1 | 1/2002 | Cimino | |
| 2002/0019649 A1 | 2/2002 | Sikora et al. | |
| 2002/0022836 A1 | 2/2002 | Goble et al. | |
| 2002/0077550 A1 | 6/2002 | Rabiner et al. | |
| 2002/0156493 A1 | 10/2002 | Houser et al. | |
| 2003/0036705 A1 | 2/2003 | Hare et al. | |
| 2003/0055443 A1 | 3/2003 | Spotnitz | |
| 2003/0204199 A1 | 10/2003 | Novak et al. | |
| 2003/0212332 A1 | 11/2003 | Fenton et al. | |
| 2003/0212422 A1 | 11/2003 | Fenton et al. | |
| 2003/0229344 A1 | 12/2003 | Dycus et al. | |
| 2004/0030254 A1 | 2/2004 | Babaev | |
| 2004/0047485 A1 | 3/2004 | Sherrit et al. | |
| 2004/0054364 A1 | 3/2004 | Aranyi et al. | |
| 2004/0092921 A1 | 5/2004 | Kadziauskas et al. | |
| 2004/0097919 A1 | 5/2004 | Wellman et al. | |
| 2004/0097996 A1 | 5/2004 | Rabiner et al. | |
| 2004/0199193 A1 | 10/2004 | Hayashi et al. | |
| 2004/0204728 A1 | 10/2004 | Haefner | |
| 2004/0260300 A1 | 12/2004 | Gorensek et al. | |
| 2005/0021065 A1 | 1/2005 | Yamada et al. | |
| 2005/0033337 A1 | 2/2005 | Muir et al. | |
| 2005/0049546 A1 | 3/2005 | Messerly et al. | |
| 2005/0070800 A1 | 3/2005 | Takahashi | |
| 2005/0143769 A1 | 6/2005 | White et al. | |
| 2005/0149108 A1 | 7/2005 | Cox | |
| 2005/0165345 A1 | 7/2005 | Laufer et al. | |
| 2005/0177184 A1 | 8/2005 | Easley | |
| 2005/0192610 A1 | 9/2005 | Houser et al. | |
| 2005/0209620 A1 | 9/2005 | Du et al. | |
| 2005/0261581 A1 | 11/2005 | Hughes et al. | |
| 2005/0261588 A1 | 11/2005 | Makin et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0079878 A1 | 4/2006 | Houser |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143795 A1 | 6/2009 | Robertson |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |

| | | | |
|---|---|---|---|
| 2009/0143803 A1 | 6/2009 | Palmer et al. | |
| 2009/0143804 A1 | 6/2009 | Palmer et al. | |
| 2009/0143805 A1 | 6/2009 | Palmer et al. | |
| 2009/0143806 A1 | 6/2009 | Witt et al. | |
| 2009/0149801 A1 | 6/2009 | Crandall et al. | |
| 2009/0270853 A1 | 10/2009 | Yachi et al. | |
| 2009/0318945 A1* | 12/2009 | Yoshimine et al. | 606/169 |
| 2009/0327715 A1 | 12/2009 | Smith et al. | |
| 2010/0004668 A1 | 1/2010 | Smith et al. | |
| 2010/0004669 A1 | 1/2010 | Smith et al. | |
| 2010/0016785 A1 | 1/2010 | Takuma | |
| 2010/0030248 A1 | 2/2010 | Palmer et al. | |
| 2010/0036370 A1 | 2/2010 | Mirel et al. | |
| 2010/0036405 A1 | 2/2010 | Giordano et al. | |
| 2010/0069940 A1 | 3/2010 | Miller et al. | |
| 2010/0158307 A1 | 6/2010 | Kubota et al. | |
| 2010/0179577 A1 | 7/2010 | Houser | |
| 2010/0187283 A1 | 7/2010 | Crainich et al. | |
| 2010/0193567 A1 | 8/2010 | Scheib et al. | |
| 2010/0298743 A1 | 11/2010 | Nield et al. | |
| 2010/0298851 A1 | 11/2010 | Nield | |
| 2010/0331869 A1 | 12/2010 | Voegele et al. | |
| 2010/0331870 A1 | 12/2010 | Wan et al. | |
| 2010/0331871 A1 | 12/2010 | Nield et al. | |
| 2010/0331872 A1 | 12/2010 | Houser et al. | |
| 2011/0009850 A1 | 1/2011 | Main et al. | |
| 2011/0015627 A1 | 1/2011 | DiNardo et al. | |
| 2011/0015631 A1 | 1/2011 | Wiener et al. | |
| 2011/0015660 A1 | 1/2011 | Wiener et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087218 A1 | 4/2011 | Boudreaux et al. | |
| 2011/0087256 A1 | 4/2011 | Wiener et al. | |
| 2011/0196286 A1 | 8/2011 | Robertson et al. | |
| 2011/0196287 A1 | 8/2011 | Robertson et al. | |
| 2011/0196398 A1 | 8/2011 | Robertson et al. | |
| 2011/0196399 A1 | 8/2011 | Robertson et al. | |
| 2011/0196400 A1 | 8/2011 | Robertson et al. | |
| 2011/0196401 A1 | 8/2011 | Robertson et al. | |
| 2011/0196402 A1 | 8/2011 | Robertson et al. | |
| 2011/0196403 A1 | 8/2011 | Robertson et al. | |
| 2011/0196404 A1 | 8/2011 | Dietz et al. | |
| 2011/0288452 A1 | 11/2011 | Houser et al. | |
| 2012/0029546 A1 | 2/2012 | Robertson | |
| 2012/0059289 A1 | 3/2012 | Nield et al. | |
| 2012/0078139 A1 | 3/2012 | Aldridge et al. | |
| 2012/0078247 A1 | 3/2012 | Worrell et al. | |
| 2012/0083783 A1 | 4/2012 | Davison et al. | |
| 2012/0083784 A1 | 4/2012 | Davison et al. | |
| 2012/0184946 A1 | 7/2012 | Price et al. | |
| 2012/0203257 A1 | 8/2012 | Stulen et al. | |

FOREIGN PATENT DOCUMENTS

| | | |
|---|---|---|
| CN | 1694649 A | 11/2005 |
| CN | 1922563 A | 2/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1433425 B1 | 6/2006 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| GB | 2032221 A | 4/1980 |
| GB | 2379878 B | 11/2004 |
| GB | 2447767 B | 8/2011 |
| JP | 6-104503 A | 4/1994 |
| JP | 2005027026 A | 1/2005 |
| JP | 2006217716 A | 8/2006 |
| WO | WO 92/22259 A2 | 12/1992 |
| WO | WO 93/14708 A1 | 8/1993 |
| WO | WO 98/37815 A1 | 9/1998 |
| WO | WO 01/54590 A1 | 8/2001 |
| WO | WO 01/95810 A2 | 12/2001 |
| WO | WO 2004/037095 A2 | 5/2004 |
| WO | WO 2005/122917 A1 | 12/2005 |
| WO | WO 2006/042210 A2 | 4/2006 |
| WO | WO 2006/058223 A2 | 6/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/130793 A1 | 10/2008 |
| WO | WO 2009/018406 A2 | 2/2009 |
| WO | WO 2009/027065 A1 | 3/2009 |
| WO | WO 2011/144911 A1 | 11/2011 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
International Search Report for PCT/US2011/024167, May 24, 2011 included in PCT Publication No. WO 2011/100303 A1 (29 pages).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 29/404,676, filed Oct. 24, 2011.
U.S. Appl. No. 13/448,175, filed Apr. 16, 2012.
U.S. Appl. No. 13/151,181, filed Jun. 2, 2011.
U.S. Appl. No. 13/369,561, filed Feb. 9, 2012.

U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.

* cited by examiner

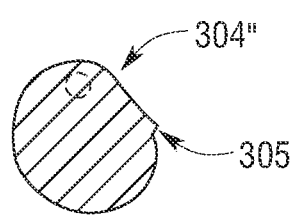 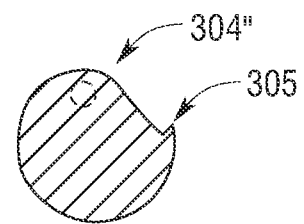
*Fig.11A*  *Fig.11B*

ULTRASONIC SURGICAL INSTRUMENT WITH COMB-LIKE TISSUE TRIMMING DEVICE

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. These devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. Those devices, however, generally lack the ability to coagulate tissue and they generally are ill-suited for trimming cartilaginous structures.

It would be desirable to provide an ultrasonic surgical instrument that overcomes some of the deficiencies of current instruments. The ultrasonic surgical instruments described herein overcome many of those deficiencies.

The foregoing discussion is intended only to illustrate some of the shortcomings present in the field of the invention at the time, and should not be taken as a disavowal of claim scope.

SUMMARY

In one general aspect, various embodiments are directed to an ultrasonic surgical instrument that may include a handle housing that has an outer sheath assembly protruding therefrom. The outer sheath assembly may have at least one distal end portion that has at least two spaced tooth members protruding therefrom. At least one ultrasonic transducer may be movably supported by the handle housing. An ultrasonic blade may protrude from the at least one ultrasonic transducer such that it is movable therewith. The ultrasonic blade may have a distal end for movement adjacent to the at least one distal end portion of the outer sheath assembly. A drive system may interact with the at least one ultrasonic transducer assembly for selectively applying an actuation motion thereto to cause the at least one ultrasonic transducer assembly to move within the handle housing.

In connection with another general aspect of the present invention, there is provided an ultrasonic surgical instrument that may include a handle housing that has an outer sheath assembly protruding therefrom. The outer sheath assembly may have a pair of spaced comb-like members that each has at least two spaced tooth members protruding therefrom. At least one ultrasonic transducer may be movably supported by the handle housing for selective axial travel therein. An ultrasonic blade may protrude from the at least one ultrasonic transducer and be axially movable therewith. The ultrasonic blade may have a distal end that is configured for movement between the pair of spaced comb-like members. A trigger may be operably coupled to the handle assembly and be configured to interact with the at least one ultrasonic transducer to selectively apply axial actuation motion thereto.

In connection with still another general aspect of the present invention, there is provided an ultrasonic surgical instrument that may include a handle housing that has an outer sheath assembly protruding therefrom. The outer sheath assembly may include a pair of spaced comb-like members that each have at least two spaced tooth members protruding therefrom. At least one ultrasonic transducer may be rotatably supported within the handle housing. An ultrasonic blade may protrude from the at least one ultrasonic transducer and may be rotatable therewith. The ultrasonic blade may have a distal end for rotation between the pair of spaced comb-like members. A trigger may be operably coupled to the handle assembly and interact with a series of gears that interfaces with the at least one ultrasonic transducer and the trigger such that actuation of the trigger causes the series of gears to apply rotational motion to the at least one ultrasonic transducer.

FIGURES

The features of various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 11A is a cross-sectional view of another non-limiting ultrasonic blade arrangement of the present invention;

FIG. 11B is a cross-sectional view of another non-limiting ultrasonic blade arrangement of the present invention;

DESCRIPTION

Figure 1:
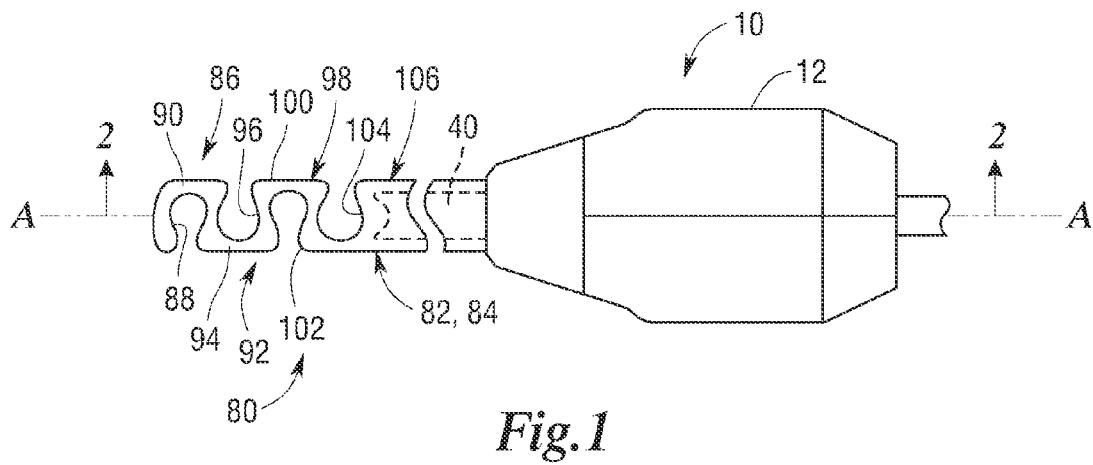
FIG. 1 is a plan view of a non-limiting surgical instrument of the present invention.

The owner of the present application also owns the following U.S. Patent Applications that were filed on even date herewith and which are herein incorporated by reference in their respective entireties:

U.S. patent application Ser. No. 12/703,860, entitled ULTRASONICALLY POWERED SURGICAL INSTRUMENTS WITH ROTATING CUTTING IMPLEMENT;

U.S. patent application Ser. No. 12/703,864, entitled METHODS OF USING ULTRASONICALLY POWERED SURGICAL INSTRUMENTS WITH ROTATABLE CUTTING IMPLEMENTS;

U.S. patent application Ser. No. 12/703,866, entitled SEAL ARRANGEMENTS FOR ULTRASONICALLY POWERED SURGICAL INSTRUMENTS;

U.S. patent application Ser. No. 12/703,870, entitled ULTRASONIC SURGICAL INSTRUMENTS WITH ROTATABLE BLADE AND HOLLOW SHEATH ARRANGEMENTS;

U.S. patent application Ser. No. 12/703,875, entitled ROTATABLE CUTTING IMPLEMENT ARRANGEMENTS FOR ULTRASONIC SURGICAL INSTRUMENTS;

U.S. patent application Ser. No. 12/703,877, entitled ULTRASONIC SURGICAL INSTRUMENTS WITH PARTIALLY ROTATING BLADE AND FIXED PAD ARRANGEMENT;

U.S. patent application Ser. No. 12/703,879, entitled DUAL PURPOSE SURGICAL INSTRUMENT FOR CUTTING AND COAGULATING TISSUE;

U.S. patent application Ser. No. 12/703,885, entitled OUTER SHEATH AND BLADE ARRANGEMENTS FOR ULTRASONIC SURGICAL INSTRUMENTS; and U.S. patent application Ser. No. 12/703,893, entitled ULTRASONIC SURGICAL INSTRUMENTS WITH MOVING CUTTING IMPLEMENT.

Various embodiments are directed to apparatuses, systems, and methods for the treatment of tissue Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Various embodiments are directed to improved ultrasonic surgical systems and instruments configured for effecting tissue dissecting, cutting, and/or coagulation during surgical procedures as well as the cutting implements employed thereby. In one embodiment, an ultrasonic surgical instrument apparatus is configured for use in open surgical procedures, but has applications in other types of surgery, such as arthroscopic, laparoscopic, endoscopic, and robotic-assisted procedures. Versatile use is facilitated by selective use of ultrasonic energy and the selective rotation of the cutting/coagulation implement and/or protective sheaths.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom", "upper" and "lower" also are used herein with respect to the clinician gripping the handpiece assembly. However, surgical instruments are used in many orientations and positions, and these terms are not intended to be limiting and absolute.

Figure 2:
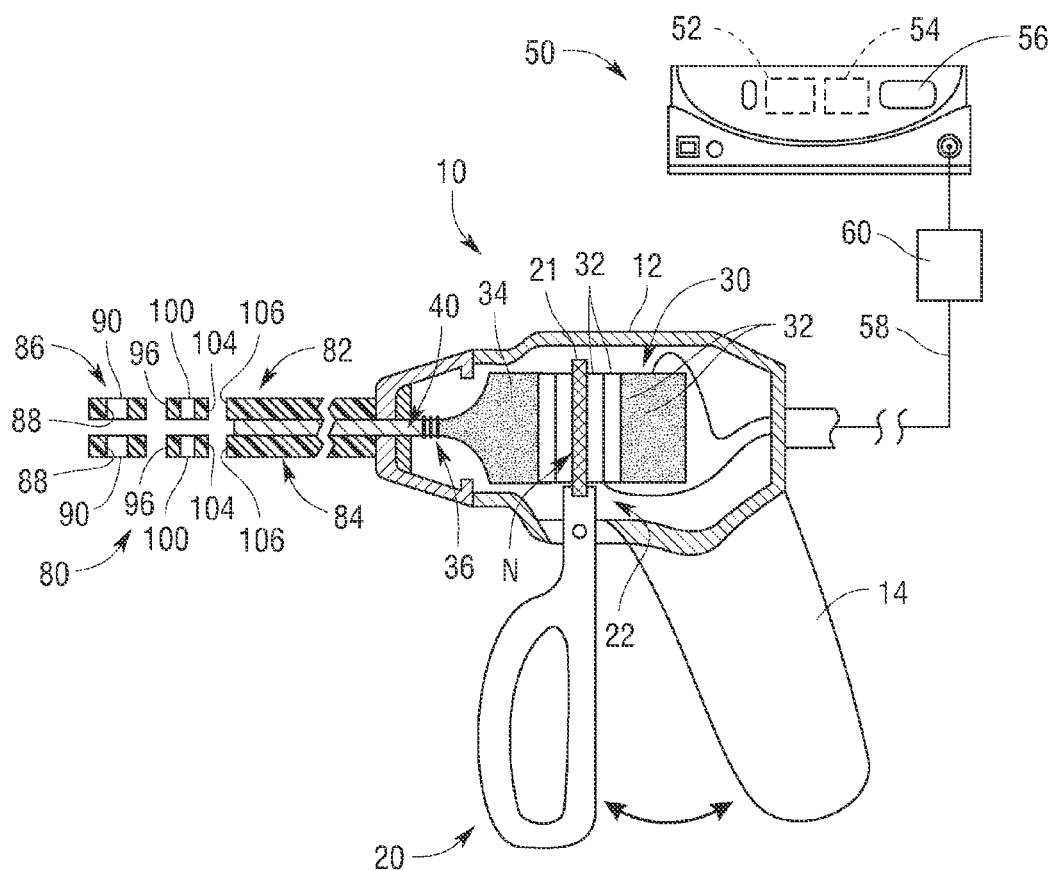
FIG. 2 is a partial cross-sectional view of the surgical instrument of FIG. 1.
Figure 3:
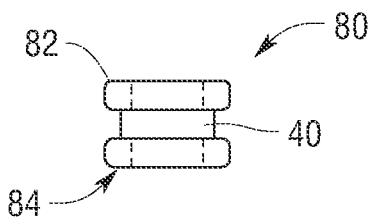
FIG. 3 is an end view of a non-limiting outer sheath assembly and ultrasonic blade arrangement of the present invention.

FIGS. 1 and 2 illustrate a surgical instrument 10 of the present invention that includes a handle housing 12 that may include a hand grip portion 14 and a drive system in the form of a movable trigger 20. In various embodiments, the housing 12 may be provided in two or more sections that are attached together by fasteners such as screws, snap features, etc. and may be fabricated from, for example, polycarbonate, polyetherimide (GE Ultem®) or metals such as aluminum, titanium or stainless steel. An ultrasonic transducer assembly 30 may be movably supported within the housing 12 for converting electrical energy to mechanical energy that results in longitudinal vibrational motion of the ends of the transducer assembly 30. The ultrasonic transducer assembly 30 may comprise at least one, and preferably a stack of, for example, four to eight ceramic piezoelectric elements or "ultrasonic transducers" 32 with a motion null point located at some point along the stack. The ultrasonic transducer assembly 30 may further include an ultrasonic horn 34 that is attached at the null point on one side and to a coupler 36 on the other side.

An ultrasonic blade 40 that may be fabricated from, for example, titanium may be fixed to the coupler 36. In alternative embodiments, the ultrasonic blade 40 is integrally formed with the ultrasonic horn 34. In either case, the ultrasonic blade 40 will vibrate in the longitudinal direction at an ultrasonic frequency rate with the ultrasonic transducer assembly 30. The ends of the ultrasonic transducer assembly 30 achieve maximum motion with a portion of the stack constituting a motionless node, when the ultrasonic transducer assembly 30 is driven at maximum current at the transducer's resonant frequency. However, the current providing the maximum motion will vary with each instrument and is a value stored in the non-volatile memory of the instrument so the system can use it.

The parts of the ultrasonic instrument 10 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the ultrasonic blade 40 of the acoustical mounting horn 34 decreases. Thus, the ultrasonic horn 34, as well as the blade/coupler, may be shaped and dimensioned so as to amplify blade motion and provide ultrasonic vibration in resonance with the rest of the acoustic system, which produces the maximum back and forth motion of the end of the acoustical mounting horn 34 close to the ultrasonic blade 40. A motion from 20 to 25 microns at the piezoelectric elements 32 may be amplified by the horn 34 into ultrasonic blade movement of about 40 to 100 microns.

The ultrasonic transducer assembly may be coupled to a source of ultrasonic control signals which may comprise a conventional ultrasonic generator 50. In various embodiments, the ultrasonic generator 50 may include an ultrasonic generator module 52 and a signal generator module 54. See FIG. 2. The ultrasonic generator module 52 and/or the signal generator module 54 each may be integrated with the ultrasonic generator 50 or may be provided as a separate circuit module electrically coupled to the ultrasonic generator 50 (shown in phantom to illustrate this option). In one embodiment, the signal generator module 54 may be integrally formed with the ultrasonic generator module 52. The ultrasonic generator 50 may comprise an input device 56 located on a front panel of the generator 50 console. The input device 56 may comprise any suitable device that generates signals suitable for programming the operation of the generator 50 in a known manner. The ultrasonic generator 50 may be coupled to the surgical instrument 10 by a cable 58. The cable 58 may comprise multiple electrical conductors for the application of electrical energy to positive (+) and negative (−) electrodes of an ultrasonic transducer assembly 30.

Various forms of ultrasonic generators, ultrasonic generator modules and signal generator modules are known. For example, such devices are disclosed in commonly owned U.S. patent application Ser. No. 12/503,770, entitled Rotating Transducer Mount For Ultrasonic Surgical Instruments, filed Jul. 15, 2007, which is herein incorporated by reference in its entirety. Other such devices are disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

In various embodiments, a foot pedal or other switching arrangement 60 may also be employed to control the application of power to the ultrasonic transducer assembly 30. When power is applied to the ultrasonic transducer assembly 30 by operation of the foot pedal 60 or other switch arrangement, the ultrasonic generator 50 may, for example, cause the ultrasonic blade 40 to vibrate longitudinally at approximately 55.5 kHz, and the amount of longitudinal movement will vary proportionately with the amount of driving power (current) applied, as adjustably selected by the user. When relatively high power is applied, the ultrasonic blade 40 may be designed to move longitudinally in the range of about 40 to 100 microns at the ultrasonic vibrational rate. Such ultrasonic vibration of the blade 40 will generate heat as the blade contacts tissue, i.e., the acceleration of the ultrasonic blade 40 through the tissue converts the mechanical energy of the moving ultrasonic blade 40 to thermal energy in a very narrow and localized area. This localized heat creates a narrow zone of coagulation, which will reduce or eliminate bleeding in small vessels, such as those less than one millimeter in diameter. The cutting efficiency of the ultrasonic blade 40, as well as the degree of hemostasis, will vary with the level of driving power applied, the cutting rate or force applied by the surgeon to the blade, the nature of the tissue type and the vascularity of the tissue.

When performing arthroscopic cutting of cartilage, the tendrils of the cartilage generally need to be trimmed flush with the surface of the bulk anatomy of the cartilaginous structure. Various embodiments of the present invention also employ a comb-like structure or outer sheath assembly 80 for capturing the cartilage tendrils in such a manner as to permit the ultrasonic blade 40 to advantageously shear off the tendrils. As used herein, the term "comb-like" refers to structures that have a plurality (at least two) tooth members that are separated by a space. As will be explained further below, the tooth members may resemble the teeth of a hair comb or, in alternative embodiments, the teeth-like members may protrude on opposite sides of the structure's central axis. As used herein, the term "comb-like" is not intended to encompass blade and/or sheath components that have standard knurled or roughened areas thereon, nor is the term "comb-like" intended to encompass a ribbed sheath or ribbed tubing.

Still referring to FIGS. 1 and 2, in one embodiment, the outer sheath assembly 80 may include a distal end portion that comprises at least one and preferably two comb-like members for capturing and positioning the cartilaginous tendrils in positions wherein they may be sheared off by the ultrasonic blade 40 as it moves axially adjacent thereto. The depicted embodiment, for example, includes an upper comb-like member 82 and a lower comb-like member 84 that is spaced from the upper comb-like member 82 to slidably receive the ultrasonic blade 40 therebetween. The upper comb-like member 82 and the lower comb-like member 84 may be fabricated from, for example, a monolithic member made of Poly-EtherEtherKetone (PEEK), Ultem®, or filled polymers such as glass filled Nylon, e.g., Grivory and each have a series of protruding tooth members that are separated by openings, such that when viewed from above (FIG. 1), the upper and lower comb-like members 82, 84 are substantially identical to each other. Alternately, the comb-like member may be fabricated from a polymer such as Teflon facing the ultrasonic member, that is backed by a stiffer, external metal member that mechanically supports the polymer member.

Figure 4:
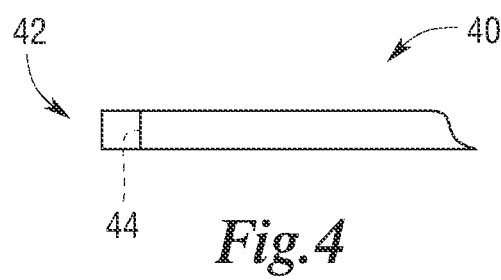
FIG. 4 is a partial side elevational view of a distal end portion of a non-limiting ultrasonic blade embodiment of the present invention.
Figure 5:
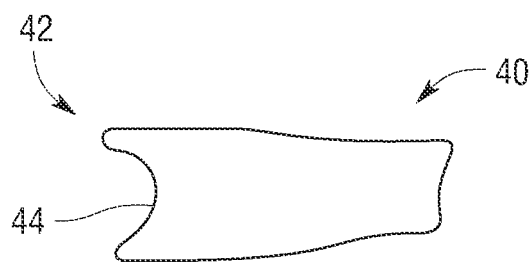
FIG. 5 is a plan view of the distal end portion of the ultrasonic blade of FIG. 4.

As can be seen in FIG. 1, for example, each of the upper and lower comb-like members 82, 84 have a series of three tooth members 86, 92, and 98 formed therein. However, other embodiments may have as few as two tooth members or more than three tooth members without departing from the spirit and scope of the present invention. The tooth members may protrude on the same side of the central axis A-A or they may protrude from alternating sides of the central axis A-A. In the depicted embodiment, the first or distal-most tooth member 86 has first opening 88 therein such that the first tooth member 86 may have a hook-like shape. A first base portion 90 of the first tooth member 86 lies on a first side of the central axis A-A defined by the outer sheath assembly 80. The second tooth member 92 has a second base portion 94 that lies on a second side of the central axis A-A. The second tooth member 92 further has a second opening 96 therein that opens on the first side of the central axis A-A. The third tooth member 98 has a third base portion 100 that lies on the first side of the central axis A-A. The third tooth member 98 further has a third opening 102 therein that opens on the second side of the central axis A-A. In addition a fourth opening 104 separates the third tooth 98 and an end 106 of the respective upper and lower comb-like members 82, 84. In the embodiment illustrated in FIG. 1, for example, the tooth members are oriented in a serpentine arrangement. In addition, as can be seen in FIGS. 4 and 5, a distal end 42 of the ultrasonic blade 40 may be substantially planar and may have an arcuate indentation 44 formed therein for contacting the tendrils that extend through the openings between the various tooth members.

As indicated above, the ultrasonic transducer assembly 30 is movably supported within the handle housing 12. In various embodiments, the handle housing 12 may be configured to support the transducer assembly 30 for selective "gross axial movement" along axis A-A. As used herein, the term "gross axial movement" is not intended to encompass that axial or longitudinal movement that is the sole result of the application of ultrasonic control signals to the ultrasonic transducers. The term "gross axial movement" as used herein encompasses that axial movement which is induced by the application of a force or axial motion to the ultrasonic transducer assembly by the applicable drive system. In the depicted embodiment, for example, the drive system comprises a manually actuatable trigger 20 that is pivotally coupled to the handle housing 12. The trigger 20 may have a yoke 22 formed thereon for engagement with a flange 21 that is centrally located at a Node "N" on the transducer assembly 30 such that when the user pivots the trigger 20 toward and away from the hand grip portion 14, the ultrasonic transducer assembly 30 and the ultrasonic blade 40 attached thereto are moved axially back and forth. Thus, in use as the ultrasonic blade 40 is moved axially between the upper and lower comb-like members 82, 84, the cartilage tendrils may be captured in the openings between the teeth. The upper and lower comb-like members 82, 84 provide opposing shearing edges that cooperate with the distal end 42 of the ultrasonic blade 40 to shear off the captured tendrils.

Figure 6:
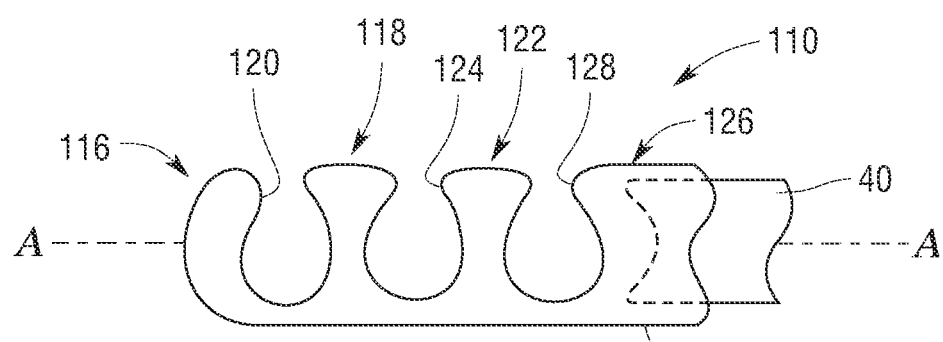
FIG. 6 is a partial plan view of a non-limiting outer sheath and ultrasonic blade arrangement of the present invention.

FIG. 6 depicts an alternative outer sheath assembly 110 that may be coupled to the housing 12 and function in a similar manner as outer sheath assembly 80 described above. The outer sheath assembly 110 may have a distal end portion that comprises an upper comb-like member 112 and a lower comb-like member 114 that is spaced from the upper comb-like member 112 to receive the insertion of the sliding ultrasonic blade 40 therebetween. The upper comb-like member 112 and the lower comb-like member 114 may be fabricated from, for example, PolyEtherEtherKetone (PEEK), Ultem®, or filled polymers such as glass filled Nylon, e.g., Grivory and each have a series of teeth members that are separated by openings such that when viewed from above, the upper and lower comb-like members 112, 114 are substantially identical to each other. As can be seen in FIG. 6, for example, each of the upper and lower comb-like members 112, 114 have a series of three teeth members 116, 122, and 128 formed therein. However, other embodiments may have as few as two teeth members or more than three teeth members without departing from the spirit and scope of the present invention. In the depicted embodiment, the first or distal-most tooth member 116 is separated from the second tooth member 118 by a first opening 120. The second tooth member 118 is separated from the third tooth member 122 by a second opening 124. The third tooth member 122 is separated from an end portion 126 of the respective upper and lower comb-like members 112, 114 by an opening 128. As can be seen in FIG. 6, all of the openings 120, 124, 128 are located on a first side of the central axis A-A. Alternately, the comb-like member may be fabricated from a polymer such as Teflon facing the ultrasonic member, that is backed by a stiffer, external metal member that mechanically supports the polymer member.

Figure 7:
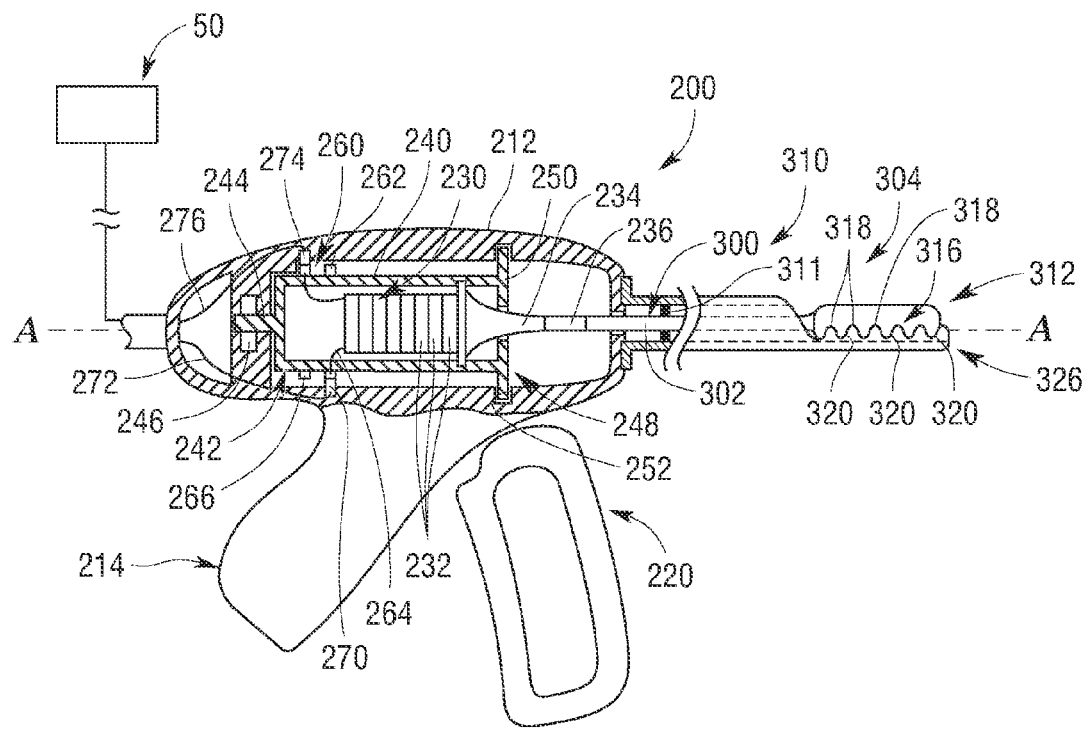
FIG. 7 is a partial cross-sectional view of another non-limiting surgical instrument embodiment of the present invention with portions of the drive system omitted for clarity.
Figure 8:
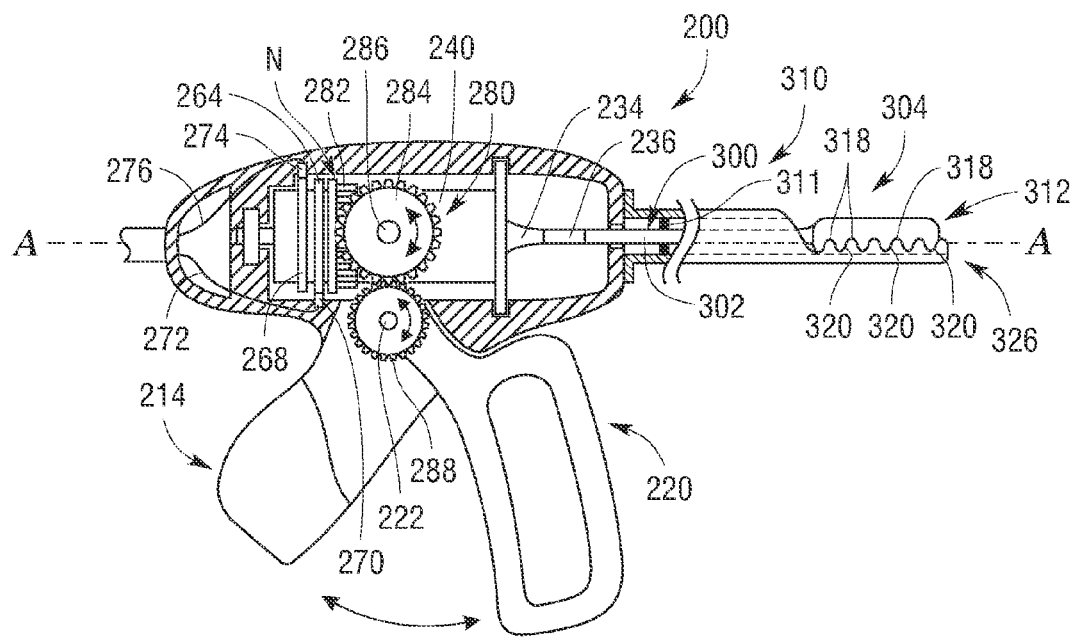
FIG. 8 is another cross-sectional view of the surgical instrument embodiment of FIG. 7.

FIGS. 7 and 8 illustrate another surgical instrument 200 of the present invention that includes a handle housing 212 that may include a hand grip portion 214 and a movable trigger 220, the purpose of which will be described in further detail below. In various embodiments, the housing 212 may be provided in two or more sections that are attached together by fasteners such as screws, snap features, etc. and may be fabricated from, for example, injection moldable polymer such as glass filled polycarbonate. A piezoelectric ultrasonic transducer assembly 230 may be movably supported within the housing 212 for converting electrical energy to mechanical energy that results in longitudinal vibrational motion of the ends of the transducer assembly 30. The ultrasonic transducer assembly 230 may comprise at least one and preferably a stack of, for example, four ceramic piezoelectric elements 232 with a motion null point located centrally along the stack. The ultrasonic transducer assembly 230 may further include an ultrasonic horn 234 that is attached at the null point on one side and to a coupler 236 on the other side. An ultrasonic blade 300 that may be fabricated from, for example, titanium, aluminum or other material with low acoustic damping may be fixed to the coupler 236. In alternative embodiments, the ultrasonic blade 300 is integrally formed with the ultrasonic horn 234.

The ultrasonic transducer assembly 230 may be supported within a transducer housing 240 that is movably supported within the housing 212. In various embodiments, the transducer housing 240 may be fabricated from, for example, aluminum or preferably a material that has a high temperature of deformation and high thermal conductivity and be configured to rotatably support the ultrasonic transducer assembly 230 within the handle housing 212. In one embodiment, for example, the proximal end 242 of the transducer housing 240 may have a shaft 244 protruding therefrom that is received within a bearing 246 supported within the housing 212. In addition, the proximal end 248 of the transducer housing 240 may have a flange 250 formed thereon that is configured to be rotatably received within a groove 252 formed in the housing 212. The ultrasonic horn 234 and coupler 236 protrude out through a opening 254 in the transducer housing 240. Thus, the transducer housing 240 is capable of rotating about axis A-A within the handle housing 212.

In various embodiments, the ultrasonic transducer assembly 230 obtains ultrasonic control signals from the source of ultrasonic control signals 50 by means of a slip ring arrangement 260. More specifically, as can be seen in FIGS. 7 and 8, a first contact ring 262 may be mounted to the perimeter of the transducer housing 240 and be coupled to the transducer assembly 230 by a conductor 264. Similarly, a second contact ring 266 may be mounted to the perimeter of the transducer housing 240 and be coupled to the transducer assembly by a conductor 266. The first contact ring 262 is positioned in sliding rotational contact with a first fixed contact 270 that is fixedly mounted within the handle housing 212 and communicates with the ultrasonic generator 50 through a conductor 272. Likewise, the second contact ring 266 is positioned in sliding rotational contact with a second fixed contact 274 that communicates with the ultrasonic generator 50 through a conductor 276. Such slip ring arrangement 260 facilitates the application of ultrasonic control signals from the ultrasonic generator 50 to the ultrasonic transducer assembly 230 while enabling the ultrasonic transducer assembly 230 to rotate about axis A-A. Other slip ring arrangements could also be employed.

Selective "gross rotation" of the transducer housing 240 and transducer assembly 230 about the central axis A-A may be accomplished through a manually-actuated drive system, generally designated as 280. As used herein, the term "gross rotation" refers to the rotation of the ultrasonic transducer assembly and ultrasonic blade that is induced by the application of a rotary actuation motion or force by the drive system and is not intended to encompass that rotary motion that may be experienced by the ultrasonic transducer assembly solely through the application of ultrasonic control signals thereto. In various embodiments, for example, the drive system 280 may comprise a first gear 282 that is mounted to the perimeter of the transducer housing 240. The first gear 282 may interface with a flange (not shown) that is centrally mounted to the stack of transducers comprising the ultrasonic transducer assembly 230. The flange and first gear 282 are thus located at a Node "N" on the transducer assembly 230. The first gear 282 may be in meshing engagement with a second drive gear 284 that is rotatably supported with the handle housing 212. For example, the second drive gear 284 may be rotatably journaled on a pin 286 that protrudes inwardly from a portion of the handle housing 212. The drive system 280 may further comprise a third drive gear 288 that is in meshing engagement with the second drive gear 284 and is coupled to the trigger 220. The trigger 220 may be pivotally mounted to the handle housing 212 about a pin 222 such that the trigger 220 may be pivoted relative to the hand grip portion 214 as illustrated by the arrows in FIG. 8. Thus, by pivoting the trigger 220 relative to the hand grip 214, the user can cause the transducer housing 240 to rotate about the central axis A-A.

Figure 9:
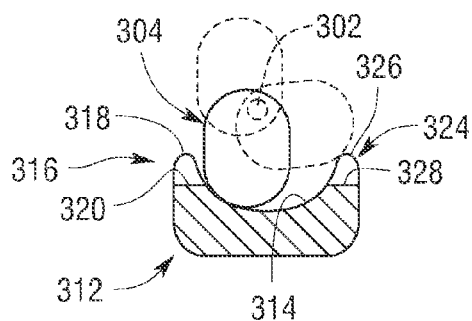
FIG. 9 is a cross-sectional view of a non-limiting outer sheath and ultrasonic blade arrangement of the present invention.
Figure 10:
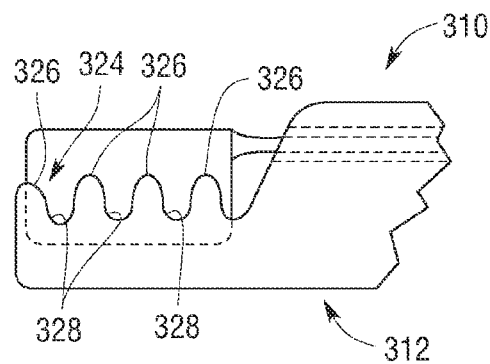
FIG. 10 is a side elevational view of a portion of the outer sheath and ultrasonic blade arrangement of FIG. 9.

Also in various embodiments, the ultrasonic blade 300 may rotatably protrude through an outer sheath 310 that is attached to the handle housing 212 or otherwise protrudes therefrom. In some embodiments, the outer sheath 310 may be fabricated from, for example, PolyEtherEtherKetone (PEEK), Ultem®, or filled polymers such as glass filled Nylon, e.g., Grivory, and have a comb-like distal end portion 312. Alternately, the comb-like member may be fabricated from a polymer such as Teflon facing the ultrasonic member, that is backed by a stiffer, external metal member that mechanically supports the polymer member. The ultrasonic blade 300 may be rotatably supported within the outer sheath 310 by one or more seals 311 that are located at a Node or Nodes along the ultrasonic blade 300. In various embodiments, one or more seals 311 of the type described in co-pending U.S. patent application Ser. No. 12/703,866, entitled SEAL ARRANGEMENTS FOR ULTRASONICALLY POWERED SURGICAL INSTRUMENTS, which has been herein incorporated by reference in its entirety may be employed. However, other seal arrangements could also be employed. As can be seen in FIGS. 9 and 10, the comb-like distal end portion 312 may form an arcuate cradle 314 that is spaced between a first lateral series 316 of spaced apart comb-like teeth 318 and a second lateral series 324 of spaced-apart comb-like teeth 326. In various embodiments, the first lateral series 316 of teeth 318 comprise at least two teeth 318 that are separated by space 320. Other pluralities of teeth 318 may be employed. The second series 324 of teeth 326 comprises a number of teeth 326 that match the number of teeth 318 and are substantially laterally aligned therewith. The teeth 326 may be separated by openings 328 as shown.

Figure 12:
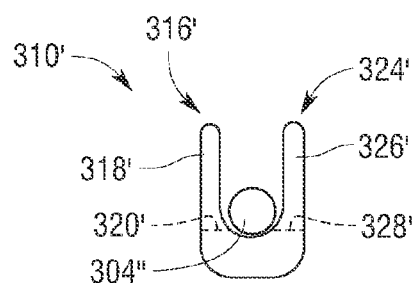
FIG. 12 is an end elevational view of another non-limiting outer sheath and ultrasonic blade arrangement of the present invention.
Figure 13:
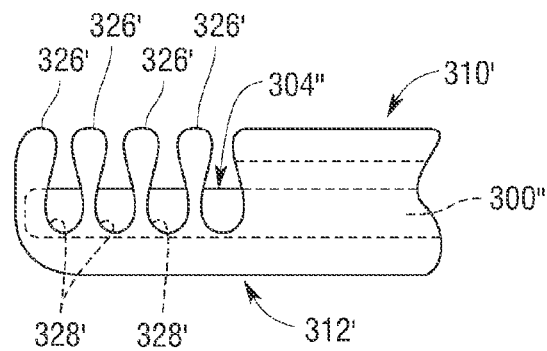
FIG. 13 is a side elevational view of the outer sheath and ultrasonic blade arrangement of FIG. 12.
Figure 11:
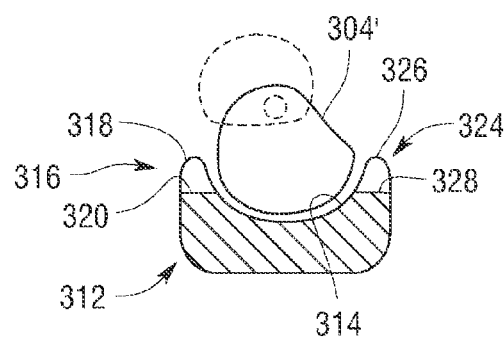
FIG. 11 is a cross-sectional view of another non-limiting outer sheath and ultrasonic blade arrangement of the present invention.

As can also be seen in FIGS. 7-10, the ultrasonic blade 300 may have a distal end portion 304 that is larger in cross-section than an elongated body portion 302 of the blade 300. The distal end portion 304 is mounted off center relative to the body section 302 as can be particularly seen in FIG. 9. Various rotational positions of the distal end portion 304 are shown in phantom lines in FIG. 9. FIG. 11 illustrates an alternative ultrasonic blade embodiment wherein the distal end 304' has an elliptical cross-sectional shape. FIGS. 11A and 11B illustrate other ultrasonic blade embodiments wherein the distal end 304" has an elliptical cross-sectional shape with a cutting tooth or notch 305 formed thereon. The notch may be a precisely machined ridge that allows the effective sharpness of the edge during ultrasonic operation to be set during manufacturing. FIGS. 12 and 13 illustrate an alternative outer sheath 310' and ultrasonic blade arrangement 300". As can be seen in those Figures, the series 316', 324' of teeth 318', 326' are longer and form a trough 314' therebetween. The first teeth 318' are separated by openings 320' and the second teeth 326' are separated by openings 328'. The distal end 304" of the ultrasonic blade 300" has a substantially round cross-section sized to rotatably fit within the trough 314'.

In use, the clinician may bring the distal end 312 of the outer sheath 310 into contact with the cartilage to be cut. Ultrasonic power may be applied to the ultrasonic transducer assembly 230 and the ultrasonic blade 230. The clinician may then pivot the trigger 220 relative to the hand grip 214 to cause the ultrasonic blade 230 to rotate. As the distal end portion 304 of the ultrasonic blade 300 rotates within the cradle 314, the distal end 304 of the blade 300 may contact the cartridge and cause the various tendrils to be "combed" between the series 316, 324 of teeth and be cut by the powered distal end portion 304 of the blade 300. In alternative embodiments, the clinician may rotate the ultrasonic blade 300 before applying ultrasonic motion thereto.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

All of the above U.S. Patents and U.S. Patent applications, and published U.S. Patent Applications referred to in this specification are incorporated herein by reference in their entirety, but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument, comprising:
   a handle housing;
   an outer sheath assembly protruding from said handle housing, said outer sheath assembly having at least one comb-like distal end portion having at least two spaced tooth members protruding therefrom;
   at least one ultrasonic transducer movably supported by said housing;
   an ultrasonic blade protruding from said at least one ultrasonic transducer and being movable therewith, said ultrasonic blade having a distal end for movement adjacent to said at least one distal end portion of said outer sheath assembly; and
   a drive system interacting with said at least one ultrasonic transducer for selectively applying an actuation motion thereto to cause said at least one ultrasonic transducer to move within said handle housing.

2. The ultrasonic surgical instrument of claim 1 wherein said outer sheath assembly has a pair of spaced comb-like distal end portions having at least two spaced tooth members and wherein said distal end of said ultrasonic blade is configured for movement between said pair of spaced distal end portions of said outer sheath assembly.

3. The ultrasonic surgical instrument of claim 1 wherein said at least two spaced tooth members on each of said comb-like distal end portions are oriented in a serpentine arrangement.

4. The ultrasonic surgical instrument of claim 1 wherein said at least one ultrasonic transducer is movably supported within said handle housing for selective gross axial travel therein.

5. The ultrasonic surgical instrument of claim 1 wherein said at least one ultrasonic transducer is movably supported within said handle housing for selective gross rotation therein.

6. The ultrasonic surgical instrument of claim 1 wherein said drive system comprises a trigger movably attached to said handle housing and interfacing with said at least one ultrasonic transducer, such that an application of an actuation motion to said trigger causes said at least one transducer to move within said handle housing.

7. The ultrasonic surgical instrument of claim 6 wherein said drive system further comprises a series of gears operably interfacing with said trigger and said at least one ultrasonic transducer.

8. The ultrasonic surgical instrument of claim 1 wherein said ultrasonic blade has an elongated central portion that has a substantially round cross-sectional shape and wherein said distal end portion of said ultrasonic blade eccentrically protrudes from said elongated central portion.

9. The ultrasonic surgical instrument of claim 1 wherein said distal end of said ultrasonic blade is substantially planar.

10. The ultrasonic surgical instrument of claim 1 wherein said distal end of said ultrasonic blade has a substantially round cross-sectional shape.

11. An ultrasonic surgical instrument, comprising:
    a handle housing;
    an outer sheath assembly protruding from said handle housing, said outer sheath assembly having a pair of spaced comb-like members each having at least two spaced tooth members protruding therefrom;
    at least one ultrasonic transducer movably supported by said housing for selective gross axial travel therein;
    an ultrasonic blade protruding from said at least one ultrasonic transducer and being axially movable therewith, said ultrasonic blade having a distal end for movement between said pair of spaced comb-like members; and
    a trigger operably coupled to said handle assembly and interacting with said at least one ultrasonic transducer to selectively apply gross axial actuation motion thereto.

12. The ultrasonic surgical instrument of claim 11 wherein said pair of spaced comb-like members are fabricated from a polymeric material.

13. The ultrasonic surgical instrument of claim 11 wherein each said comb-like member defines a central axis wherein at least one of said tooth members protrudes on one lateral side of said central axis and wherein another one of said tooth members protrudes from another lateral side of said central axis.

14. The ultrasonic surgical instrument of claim 11 wherein said distal end of said ultrasonic blade is substantially planar and has an arcuate indentation formed therein.

15. An ultrasonic surgical instrument, comprising:
    a handle housing;
    an outer sheath assembly protruding from said handle housing, said outer sheath assembly having a pair of spaced comb-like members that each have at least two spaced tooth members protruding therefrom;
    at least one ultrasonic transducer supported within said handle housing for gross rotation therein;
    an ultrasonic blade protruding from said at least one ultrasonic transducer and being rotatable therewith, said ultrasonic blade having a distal end for rotation between said pair of spaced comb-like members;

a trigger operably coupled to said handle housing; and a series of gears interfacing with said at least one ultrasonic transducer and said trigger such that actuation of said trigger causes said series of gears to apply gross rotational motion to said at least one ultrasonic transducer.

16. The ultrasonic surgical instrument of claim 15 wherein said at least one ultrasonic transducer is supported within a transducer housing that is supported for gross rotation within said handle housing and wherein said series of gears comprises:

a first driven gear supported on said transducer housing;

a second driven gear in meshing engagement with said first driven gear; and a third drive gear supported by said trigger and in meshing engagement with said second driven gear.

17. The ultrasonic surgical instrument of claim 16 further comprising a slip ring assembly interfacing between a source of ultrasonic control signals and said at least one ultrasonic transducer.

18. The ultrasonic surgical instrument of claim 17 wherein said slip ring assembly comprises:

a first fixed contact supported on said handle housing and communicating with said source of ultrasonic control signals;

a second fixed contact supported on said handle housing and communicating with said source of ultrasonic control signals;

a first movable contact on said transducer housing, said first movable contact in moving contact with said first fixed contact and communicating with said at least one ultrasonic transducer; and a second movable contact on said transducer housing, said first movable contact in moving contact with said second fixed contact and communicating with said at least one ultrasonic transducer.

19. The ultrasonic surgical instrument of claim 15 wherein said ultrasonic blade has an elongated central portion having a substantially round cross-sectional shape and wherein said distal end portion eccentrically protrudes from said elongated central portion.

20. The ultrasonic surgical instrument of claim 19 wherein said distal end portion of said ultrasonic blade has an elliptical cross-sectional shape.

\* \* \* \* \*